United States Patent
Heidenau et al.

(10) Patent No.: US 9,402,933 B2
(45) Date of Patent: Aug. 2, 2016

(54) STRUCTURED COATINGS FOR IMPLANTS AND PROCESS FOR THE PREPARATION THEREOF

(75) Inventors: Frank Heidenau, Pegnitz (DE); Gunter Ziegler, Nürnberg (DE)

(73) Assignee: BioCer Entwicklungs GmbH, Bayreuth (DE)

( * ) Notice: Subject to any disclaimer, the term of this patent is extended or adjusted under 35 U.S.C. 154(b) by 699 days.

(21) Appl. No.: 12/310,499

(22) PCT Filed: Aug. 31, 2007

(86) PCT No.: PCT/EP2007/059115
§ 371 (c)(1),
(2), (4) Date: Aug. 21, 2009

(87) PCT Pub. No.: WO2008/025840
PCT Pub. Date: Mar. 6, 2008

(65) Prior Publication Data
US 2009/0317766 A1 Dec. 24, 2009

(30) Foreign Application Priority Data
Sep. 1, 2006 (DE) .......................... 10 2006 041 023

(51) Int. Cl.
| | |
|---|---|
| *A61L 27/32* | (2006.01) |
| *A61L 27/30* | (2006.01) |
| *A61L 27/44* | (2006.01) |
| *A61L 27/46* | (2006.01) |
| *A61L 27/56* | (2006.01) |
| *A61L 27/60* | (2006.01) |

(52) U.S. Cl.
CPC ............... *A61L 27/32* (2013.01); *A61L 27/306* (2013.01); *A61L 27/446* (2013.01); *A61L 27/46* (2013.01); *A61L 27/56* (2013.01); *A61L 27/60* (2013.01)

(58) Field of Classification Search
CPC ....... A61L 27/306; A61L 27/32; A61L 27/60; A61L 27/46; A61L 27/56; A61L 27/446
See application file for complete search history.

(56) References Cited

U.S. PATENT DOCUMENTS

| | | | |
|---|---|---|---|
| 6,663,662 B2 * | 12/2003 | Pacetti ...................... | A61F 2/07 623/1.13 |
| 2006/0161256 A1 * | 7/2006 | Ziegler et al. ............. | 623/11.11 |
| 2007/0059379 A1 | 3/2007 | Gerber | |
| 2007/0196419 A1 | 8/2007 | Teller et al. | |
| 2010/0016502 A1 * | 1/2010 | Rentrop et al. ............. | 524/588 |

FOREIGN PATENT DOCUMENTS

| | | | |
|---|---|---|---|
| DE | 10 2004 01241 | | 9/2005 |
| DE | 600 22 197 T2 | | 3/2006 |
| DE | 102 43 132 B4 | | 9/2006 |
| EP | 1 882 722 | * | 1/2008 |
| EP | 1882722 | | 1/2008 |
| WO | WO 2004/026346 | | 4/2004 |
| WO | WO 2004/103421 | | 12/2004 |

OTHER PUBLICATIONS

Notification of Transmittal of Translation of the International Preliminary Report on Patentability corresponding to International Patent Application No. PCT/EP2007/059115 dated Mar. 26, 2009.
Hoffmann et al, "Corrosion behaviour, metal release and biocompatibility of implant materials coated by $TiO_2$-sol gel chemistry" Biomedizinische Technik, Fachverlag Schiele and Schoen Gmbh, Berlin, DE, vol. 50, No. 10, pp. 320-329 (Jan. 1, 2005). (English Abstract).
Heidenau et al, "A novel antibacterial titania coating: Metal ion toxicity and in vitro surface colonization" Journal of Materials Science: Materials in Medicine, Kluwer Academic Publishers, BO, vol. 16, No. 10, pp. 883-888 (Oct. 1, 2005).
Jokinen et al., Influence of sol and surface properties on in vitro bioactivity of sol-gel-derived $TiO_2$ and $TiO_2$-$SiO_2$ films deposited by dip-coating method. *J. Biomed Mater Res.* 42 (1998) 295-302.
Teller et al., "Antibiotic loaded sol-gel derived calcium phosphate/silica composite for bone preparation." *Key Engineering Materials*, vols. 284-286 (2005) 415-418.
Huesing & Schubert, "Aerogels—Airy Materials: Chemistry, Structure, and Properties", *Angew. Chem. Int. Ed.*, vol. 37, No. 1-2, Feb. 2, 1998, pp. 22-45.

* cited by examiner

*Primary Examiner* — Suzanne Ziska
(74) *Attorney, Agent, or Firm* — Jenkins, Wilson, Taylor & Hunt, P.A.

(57) ABSTRACT

The invention relates to a method for producing a powder-filled ceramic coating made from a precursor ceramic compound (for example, a sol-gel), said coating having an advantageous surface roughness and wherein active ingredients may be eluted from the matrix or filler under physiological conditions and to an implant which can be produced according to the claimed method.

36 Claims, 4 Drawing Sheets a)

b)

a)  b)  c)

STRUCTURED COATINGS FOR IMPLANTS AND PROCESS FOR THE PREPARATION THEREOF

Figure 1:
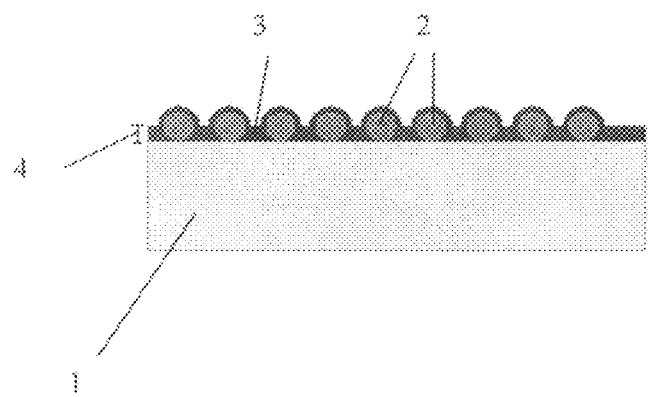
Figure 1:
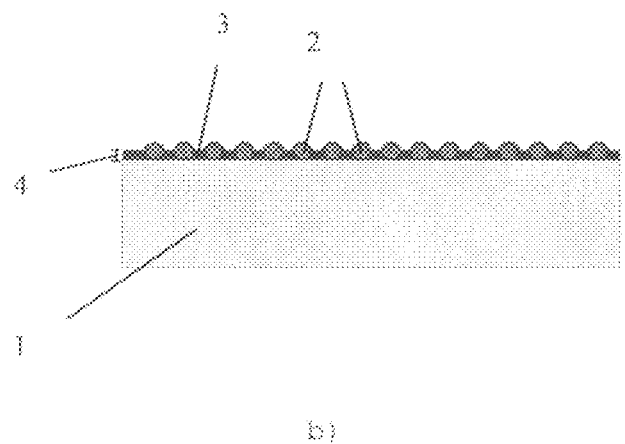

The present invention relates to a process for the preparation of a powder-filled ceramic coating on an implant, and to a coated implant.

BACKGROUND OF THE INVENTION AND PRIOR ART

The surface properties of an implant are crucial to the bioacceptability and the biocompatibility of the implant. Firstly, the texture or morphology of the surface is crucial for the growth of new cells on the implant. Secondly, the growth of desired cells can be encouraged by releasing active substances, or the growth of undesirable cell clusters, such as introduced bacteria, which may lead to an infection or even cause the implant to be rejected, can be inhibited.

For these reasons, coatings which are produced in sol-gel processes and release active substances have been developed in the prior art. This release of active substances may have an antibacterial effect for example, as disclosed in DE 10243132. However, the use thereof is limited to metal ions, the organic salts of which can be dissolved in a sol.

In an attempt to adapt the texture of an implant to natural conditions, WO 2004/103421 A1 discloses a bone substitute material in the form of a granular material which is formed using a calcium phosphate powder in a sol-gel process. This granular material can be coated onto an implant but must, however, be applied by an expensive method, a plasma spraying method for example.

A similar material is disclosed in application DE 10 2004 012411 A1 by DOT Coating. Application as a layered system with a defined surface texture is not described. It is also not possible to texture the surface in a targeted manner. In addition, the material contains a polysilicic acid-based composite material which contains an organic polymer. However, this material has the drawback that it has a reduced stability in storage on account of the organic components and is difficult to sterilise with the γ-radiation sterilisation method which is conventional in the medical field. A subsequent sterilisation procedure in hospital is also hindered by the fact that heating the material to 132° C. results in degradation of the organic components. Furthermore, an active substance, such as an antibiotic or a polymer, present in the material can be damaged or immobilised by radicals produced by γ-radiation.

DE 102 43 132 B4 discloses an antimicrobial titanium oxide coating for implants which is prepared in a sol-gel process. In this application, the metal salt used is homogeneously and completely dissolved in the sol-gel matrix and is not present as solid particles, and it is therefore not possible to texture the surface.

DE 600 22 197 T2 discloses a material, for example, in the form of particles which are prepared in a sol-gel process. Adding particles while carrying out the sol-gel process is not mentioned. In addition, the material must be heated to temperatures of 800 to 1,500° C. for hardening purposes.

A simple sol-gel coating without a powder filler is known from the publication by M. Jokinen et al., *J. Biomed. Mater. Res.*, 42 (1998) 295-302.

Finally, a porous material which can be charged with antibiotics to produce an antimicrobial element is known from M. Teller et al., Key Engineering Materials, Vols. 284-286 (2005), pages 415-418. This material is not suitable for coating an implant due to the high porosity of the material.

All the aforementioned processes have the drawback that it is not possible to texture the surface in a purposeful manner and to adjust the release of the active substance.

The object of the present invention is therefore to provide a process for preparing a coating which enables the surface texture morphology of a coating on a substrate to be adjusted in a purposeful manner, it also being possible to adjust the release of an active substance.

SUMMARY

This object is achieved by a process for preparing a particle-filled, metal oxide coating on an implant, comprising the following steps:
  a. providing a mixture of an organic solvent and a organometallic precursor;
  b. adding a particle-shaped filler to the mixture from step a. in order to prepare a preparation;
  c. applying the preparation prepared in step b. to an implant to provide a coating on the implant; and
  d. drying the coating applied.

DETAILED DESCRIPTION OF THE INVENTION

A process for producing a filled, biocompatible metal oxide coating on an implant, with which process an implant can be produced, is provided according to the invention. Under physiological conditions, active substances can be released from the coating and/or the filler into the environment.

According to a first aspect, the present invention provides a process for preparing a particle-filled, metal oxide coating on an implant, comprising the following steps:
  a. providing a mixture of an organic solvent and a organometallic precursor;
  b. adding a particle-shaped filler to the mixture from step a. in order to prepare a preparation;
  c. applying the preparation prepared in step b. to an implant to provide a coating on the implant; and
  d. drying the coating applied.

The process according to the invention for coating substrates, in particular implants, comprises the following steps. A mixture is initially prepared, said mixture being a low-viscosity suspension, what is known as a sol, containing an organic solvent, an organometallic compound and optionally water and/or an acid. A filler is added to this mixture.

A dispersant is added, in part to ensure that the filler is distributed in a finely dispersed manner. This dispersant may be, for example, an alkylol ammonium salt of low-molecular carboxylic acids, a copolymer with acid groups, a solution of copolymers with pigment affine groups, an acrylate copolymer with pigment affine groups, a high-molecular block copolymer with pigment affine groups or a solution of acrylate copolymers with basic pigment affine groups.

The term "sol" is to be understood according to the invention as a colloidal solution, in which a solid substance is dispersed in a liquid medium in a very finely dispersed manner without aggregate formation, i.e. it is dispersed at a substantially molecular or atomic level (diameter of the sol particles <30 nm, preferably <10 nm). The sol may also be termed a nanosuspension since the organometallic compounds are dispersed on a nanometre scale. The oxide coating produced from the sol in a sol-gel process is termed a matrix or an oxide matrix.

The term "filler" is to be understood according to the invention as an addition in a particular form which either acts as a texture-providing element and/or has a therapeutic effect by releasing active substances. The filler may be stable or degradable under physiological conditions. Metals, metal alloys, glass, ceramics, inorganic active substances, sparingly soluble salts, in particular crystals of sparingly soluble salts, or combinations thereof may be used as fillers.

The particle-shaped fillers may be impermeable or porous or have different degrees of porosity, i.e. may have a porosity gradient. It is also possible for the filler to be resorbable in part.

Examples of the metals and metal alloys which may preferably be used according to the invention as fillers are elemental metals such as silver, copper, calcium, magnesium or zinc, and metal alloys such as brass.

Examples of the ceramic materials or ceramics which may preferably be used according to the invention as fillers are oxides or nitride such as aluminium oxide, zirconium oxide, titanium oxide, silicon oxide, calcium phosphate, hydroxyl apatite for example, glass and glass ceramics, preferably glass and glass ceramics which dissolve or disintegrate under physiological conditions.

The term "active substance" is to be understood as both ions of the elements from which the filler is formed, and organic or inorganic therapeutically active ingredients which are physically or chemically bound to the filler or are encapsulated in the active substance. Examples of ions are calcium, zinc, silver, copper or magnesium ions. Particles which contain these ions or can release these ions may also be used.

The active substance may also be released from the oxide matrix. In addition, a metal ion in the form of a metal salt may for example be added to the sol. When the sol is applied to a substrate, the metal ions are introduced into the matrix and are released again under physiological conditions. Metal salts of this type are introduced in addition to the fillers.

The term "implant" is to be understood according to the invention as a substrate which is suitable to be implanted into a patient, i.e. in the field of human medicine, or into an animal, i.e. in the field of veterinary medicine. Examples of these implants are catheters, osteosynthesis material, endoprostheses, external/internal fixators, nails, screws and/or wires, heart valves, synthetic blood vessels and shunts, facial surgery/plastic implants, middle ear implants, dental implants, etc.

The term "physiological and pathophysiological conditions" is to be understood according to the invention as conditions which prevail in the environment of an implant implanted into a patient. The term includes, according to the invention, all body fluids which may come into contact with an implanted implant of this type, but also other buffer solutions which may be used to replace body fluids, such as a physiological saline solution, phosphate-buffered saline (PBS), irrigation solutions, disinfectant solutions and the like.

A purely inorganic coating is preferably produced by the process. This inorganic coating is free of organic materials, such as organic solvents or organic polymer compounds. Organic material contained in the coatings may possibly be removed by a thermal heating process, for example a firing process.

The thickness of the coating according to the invention is in the range of several hundred nanometres, preferably approximately 50 to 10,000 nm, preferably 100 to 5,000 nm, more preferably 150 to 1,500 nm. The particular thin nature of the layer and the low proportion of filler material in the layer enable the adhesion of the layer to the substrate to be improved significantly.

The size of the filler particles should not exceed a maximum value. The matrix, produced from the organometallic precursor or progenitor, acts as an adhesive which covers the substrate and surrounds the filler particles. The size of the filler particles should not be more than five times, preferably three times, greater than the thickness of the matrix. If the particle size is greater than five times the thickness of the matrix, the resulting coating is not fixed sufficiently to be substrate and can become detached when loaded.

The ratio of particle size to layer thickness of the matrix enables the roughness of the surface to be adjusted in a purposeful manner. A filler-particle:matrix thickness ratio of this type causes the filler particles to project out of the coating and to form an uneven surface which is rough on a micro-scale. The $R_a$ values for the surfaces are preferably between 0.01 and 10 μm, preferably 0.1 to 5 μm, more preferably 0.2 to 1.5 μm. Cells can populate this rough surface better than the conventional smooth or shot-blasted implant surfaces.

The introduction of particle-shaped fillers enables the surface to be textured. This texture may be produced in a purposeful manner in the form of microroughness, for example with the aforementioned surface roughness, by the particle size, the particle size distribution and the particle quantity.

The size of the filler particles is preferably between 0.01 and 10 μm, preferably between 0.1 and 5 μm, most preferably between 0.2 and 1.5 μm. The size of the filler particles is distributed within a narrow range of sizes. In this case, the $d_{50}$ value of the particles is preferably less than 3.5 μm, preferably less than or equal to 3 μm, more preferably less than or equal to 2 μm. The $d_{50}$ value indicates the particle size below which the sizes of 50% of all the particles fall. In this way, a homogeneous surface with even surface roughness can be achieved.

The filler content is in the range of up to 15% by weight, preferably between 0.005 and 10% by weight, more preferably between 0.01 and 8% by weight and even more preferably between 0.1 and 1% by weight. The amount added is therefore based on the total weight of precursor material and solvent, which together represent 100%.

The term "thickness of the matrix" should be understood as merely the thickness of the oxide matrix resulting from the sol-gel process. In contrast, the thickness of the entire coating also includes the particles introduced. The particles are embedded in the matrix, which is preferably between 20 and 500 nm, preferably between 50 and 300 nm, and more preferably between 20 and 200 nm thick. In this respect, the ratio between the particle size and matrix thickness should also be taken into account, as mentioned above.

According to a preferred embodiment of the invention, the coating process can be carried out a number of times. In this case, a layer with a thickness in the aforementioned range is applied each time. The total thickness of the plurality of layers is then a multiple of the thickness of the individual layers, i.e. the layer thickness range is then a multiple of the aforementioned thicknesses for a single layer. The fillers in the different layers may be different or the same. The concentration may also vary from layer to layer in order to achieve a gradient for the release of active substances. It is also possible to charge the different layers with different active substances in such a way that a substance with an antimicrobial effect is initially released for example and then, after a predetermined period of time, an active ingredient which promotes bone growth is released. In this way, the release of active substances at different times can be adapted individually to different requirements.

Metal implants, implants made of metal alloys, plastics material, glass, ceramic implants, composite materials, bone substitute materials or a combination thereof may be used according to the invention as implants. Examples of preferred implants are catheters, osteosynthesis plates, endoprostheses, external/internal fixators, nails, screws and/or wires, heart valves, synthetic blood vessels and shunts, facial surgery/plastic implants, middle ear implants and dental implants.

Examples of metals and metal alloys which may preferably be used according to the invention for implants are titanium, steel, iron, and/or steel alloys, iron alloys, titanium alloys, preferably TiAl6V4 or TiAl6Nb7, cobalt-chromium base alloys and/or osteosynthesis steel, preferably AlSI316L, and elementary metals such as silver, copper, calcium, magnesium or zinc.

Examples of plastics materials which may preferably be used according to the invention for implants are polymers such as polyethylene, polypropylene, polytetrafluoroethylene, polyethylene terephthalate, polyamides, polyurethanes, polysiloxanes, polysiloxane elastomers, polyetheretherketones, polysulphone, polysaccharides and polylactides.

Examples of ceramic materials which may preferably be used according to the invention for implants are oxides or nitrides such as aluminium oxide, zirconium oxide, titanium oxide, silicon oxide, calcium phosphates, for example hydroxyl apatite, and glass and glass ceramics, preferably glass and glass ceramics which dissolve or disintegrate under physiological conditions.

Autografts, allografts, xenografts or synthetic bone substitute materials may preferably be used as bone replacement materials.

The mixture which contains the filler and has a viscosity corresponding virtually to that of water is applied to the substrate. This may be achieved by dip coating, spin coating, application by doctor blade, printing or spraying or other methods according to the prior art.

The precursors contained in the mixture are preferably multicoordinated, organometallic compounds with —OR ligands, which are coordinated to the metal by the oxygen atom, R being a linear or branched alkyl residue with a preferred chain length from C2 to C8. Alternatively, or in addition, unsaturated alkyl residues (alkenyl residues) and/or oxygen-containing and/or nitrogen-containing alkyl residues or alkenyl residues which also preferably have from 2 to 8 C-atoms, but also longer alkyl chains up to C-12 in length, may also be used according to the invention for specific applications such as UV hardenability. Examples of suitable oxygen-coordinated alkyl residues are, in particular, ethyl-, n-propyl-, isopropyl-, n-butyl-, isobutyl-, n-pentyl-, and/or isopentyl residues.

Examples of suitable alkenyl residues are acrylate, methacrylate or longer-chained alkyl chains or branched alkyl chains with double bonds. The preferred length of the main chain is C2 to C12, and the preferred length of the side chains is C2 to C6.

Examples of suitable O-substituted and N-substituted alkyl and/or alkenyl residues are carbon-chain-based residues which satisfy the aforementioned requirements but which also contain ether groups, keto groups or amino groups.

Examples of precursors which may be used according to the invention are tetrabutoxy titanate, titanium isobutoxy titanate, titanium tetrapropylate, titanium tetraisopropylate, titanium tetraacetyl acetonate, titanium tetraethoxy titanate or the corresponding substances based on silicon, zirconium or aluminium, provided that they are chemically stable. The term "metal oxides" should therefore be understood as referring in particular to the oxides of the aforementioned metals titanium, silicon, zirconium and aluminium.

Linear or branched alcohols with chain lengths of 2 to 8 carbon atoms are preferably used as the organic solvent, for example ethanol, propanol, isopropyl alcohol, n-butanol, sec-butanol or combinations of the aforementioned alcohols, ethanol and n-butanol being particularly preferred. Further organic solvents which may be used according to the invention are cyclic, aromatic and/or heteroaromatic hydrocarbons or the derivatives thereof, for example cyclopentane, cyclohexane, benzene, toluene, tetrahydrofuran or dioxane, benzene, toluene and/or tetrahydrofuran being particularly preferred. The organic solvent can be selected by the person skilled in the art in accordance with the metal salt or the organometallic compound used. Any mixtures of the aforementioned solvents may also be used according to the invention.

Water and/or an acid, preferably a mineral acid may optionally also be contained in the preparation. Nitric acid is preferably used as a mineral acid. However, in addition or as an alternative thereto, other acids such as hydrochloric acid, sulphuric acid, phosphoric acid, or organic acids such as citric acid, trifluoroacetic acid or acetic acid may be used.

If an acid is used, the concentration of the acid is preferably 1 to 50 mole %, preferably 2 to 20 mole %, more preferably 8 to 10 mole %, of the organometallic precursor used.

The concentration of the solvent is preferably 5 to 50 times, more preferably 15 to 40 times, even more preferably 20 to 35 times, the molar amount of the organometallic precursor.

While or after the aforementioned preparation, preferably in the form of a sol, is applied to the substrate, it is possible in accordance with the invention to convert said sol into a solidified, dimensionally-stable but easily deformable system or gel by evaporating the solution and/or by adjusting the stoichiometric educt ratios, the fillers being dispersed homogeneously in a solidified system or gel.

A drying procedure is then carried out, after which the coated implant can be used directly. Drying may take place in an oxygen, nitrogen, argon or air atmosphere. The drying procedure is preferably carried out between room temperature (25° C.) and 100° C., more preferably between room temperature and 50° C. Said drying procedure may take place under atmospheric pressure or reduced pressure (vacuum). It is also possible to carry out the drying process as a freeze-drying procedure or under supercritical drying conditions. The subsequent heat treatment is carried out for the purposes of mechanical stabilisation or densification of the coatings, for example heating the coating to approximately 500° C. may preferably cause the coating to ceramise. If the implant is made of plastics material, said implant is preferably heated less strongly.

This may be followed by a process of heating the coating to between 100 and 1,000° C., preferably between 200 and 800° C., more preferably between 400 and 600° C. This heating procedure can be carried out separately from or in conjunction with the drying procedure. The residence time of the substrate with the applied coating is in this case not as crucial as the temperature itself. The residence time may depend, for example, on the type of substrate and the behaviour of the substrate during the heating process. More robust substrates, such as ceramics, may be heated and cooled more quickly than metals for example which expand more during heating. However, the temperature obtained is crucial since the matrix changes if the temperature limits are exceeded.

The drying step is optionally performed under supercritical conditions, preferably in an autoclave. The term "supercritical conditions", as used in this document, is to be understood as a pressure-temperature-time profile at a predetermined autoclave volume, in which the solvent used is converted from the liquid to the gaseous state by means of density reduction beyond the physically defined critical point and thus removed from the layer without the formation of a phase boundary.

The particular advantages of this process are that the gel-type nanometre-scale pore structure which is typical of gels can be retained and thus a very highly specific coating surface can be formed. This makes it possible firstly to further influence the kinetics of the release of ions from the fillers and secondly to have a positive effect on the growth of body cells such as osteoblasts or fibroblasts, by forming a textured, porous surface.

The process according to the invention enables the concentration of active substances eluted from the coating to be precisely established by dilution or by providing a plurality of layers. Providing a plurality of layers can boost the effect of the coating, since a greater amount of active substances can be provided. A single and/or two-layer coating is preferred.

A multiple layer coating is produced according to the invention by repeating the aforementioned steps a to d, i.e. providing the mixture, preparing the preparation, applying the prepared preparation to an implant and drying the applied coating, one or more times in such a way that one or a plurality of additional layers are produced on the implant. A process of heating the implant to a temperature of between 100 and 1,000° C. may optionally be carried out each time the aforementioned method steps have been completed or once at the end of the process.

The fillers or active substances are also dispersed homogeneously in each individual coating in the case of a multi-layered coating.

Several examples will be described below but are not intended to limit the scope of the invention.

Reference is made to the following figures in the examples:

FIG. 1 is a schematic representation of the coating. By introducing fillers of different particle sizes and in different amounts, the surface morphology can be adapted in a purposeful manner or the active substances can be released in a purposeful manner. FIG. 1 shows a substrate with an oxide matrix 3, in which filler particles 2 are held, applied thereon. In this case, the diameter of the filler particles does not exceed five times the thickness 4 of the oxide matrix. The different sizes of filler particles enable different degrees of surface roughness to be achieved, as is evident by comparing FIGS. 1a) and 1b).

Figure 2:
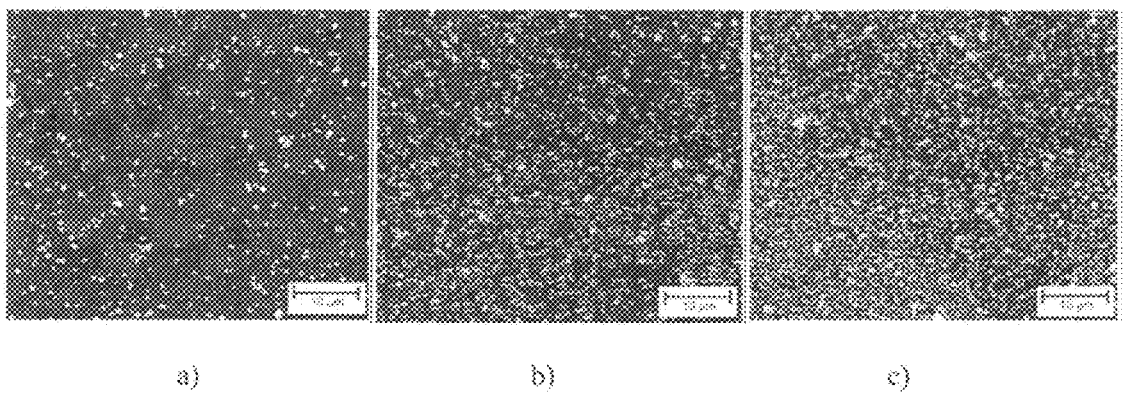

FIG. 2 shows electron microscope images of coated surfaces containing different amounts of calcium phosphate powder (hydroxyl apatite). The images show filler contents of 1 (FIG. 1a), 3 (FIG. 1b) and 8% by weight (FIG. 1c), based on the total weight of sol provided, which were produced in accordance with example 1.

Figure 3:
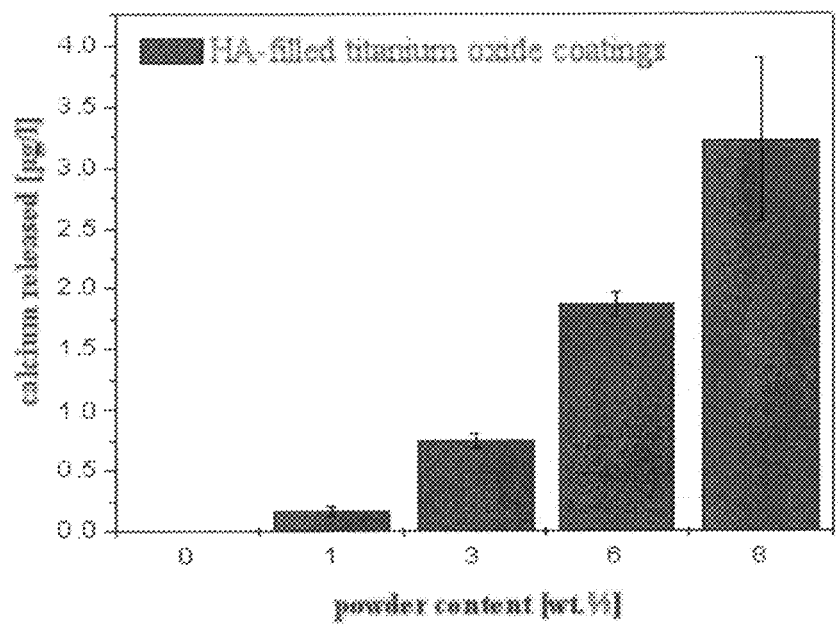

FIG. 3 shows the release of calcium irons from coatings, which were filled with different amounts of calcium phosphate powder (hydroxyl apatite), under physiological conditions (cf. FIG. 2). The polystyrene (PS) of the petri dish was used as a reference material (100%).

Figure 4:
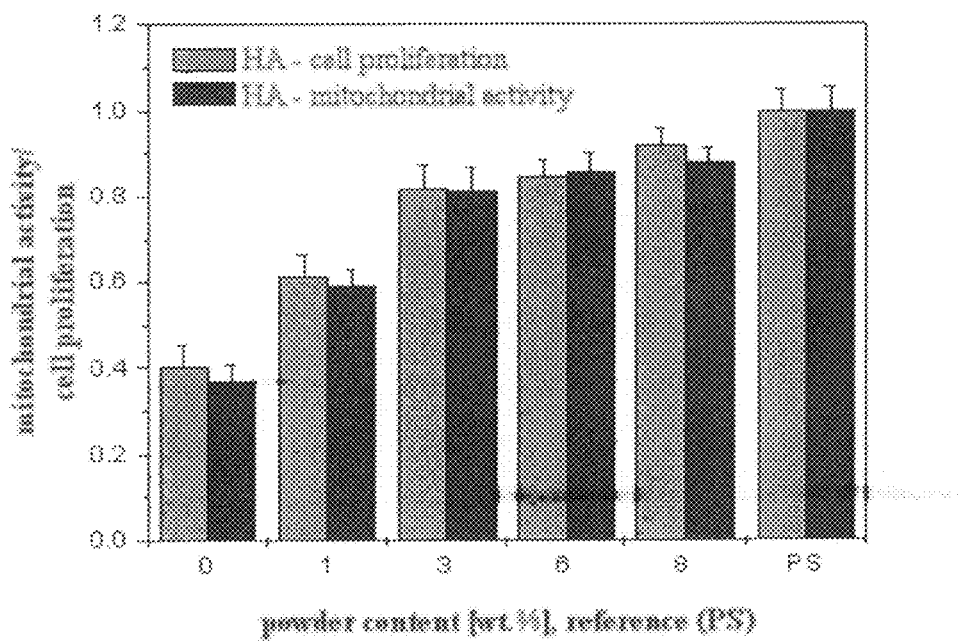

FIG. 4 shows the change in cell count of foetal mouse osteoblasts (MC3T3-E1) after being cultured for 48 hours on coatings which were filled with different amounts of calcium phosphate powder (hydroxyl apatite) (cf. FIG. 2).

Figure 5:
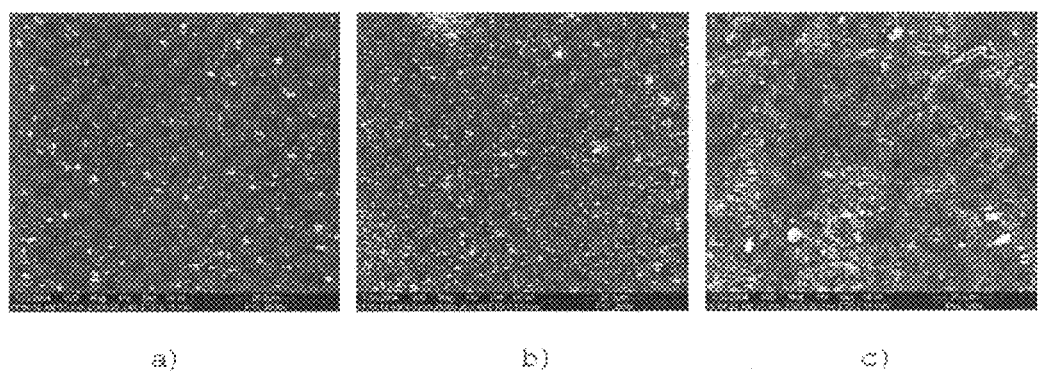

FIGS. 5a) to 5c) of FIG. 5 show electron microscope images of coated surfaces containing different amounts of titanium oxide powder. The images show filler contents of 0.5 (FIG. 5a), 3 (FIG. 5b) and 6% by weight (FIG. 5c), based on the total weight of the sol provided.

Figure 6:
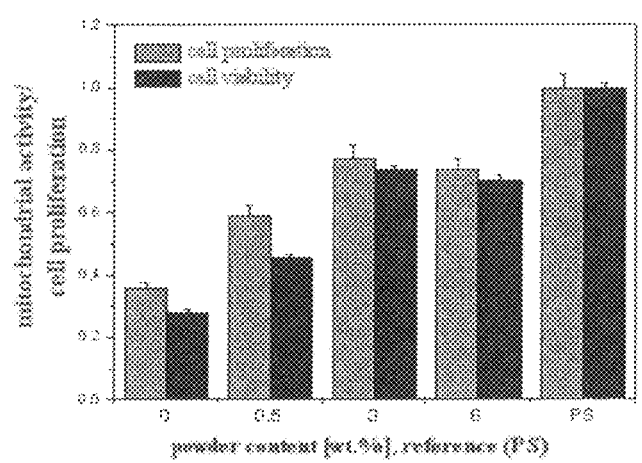

FIG. 6 shows the change in cell count and mitochondrial activity of foetal mouse osteoblasts (MC3T3-E1) after being cultured for 48 hours on coatings filled with different amounts of titanium oxide powder (cf. FIG. 5).

EXAMPLES

Example 1

Coating with a Hydroxyl Apatite Filler 69.5 g of tetrabutoxy titanate were dissolved in 500 g of n-butanol at room temperature and were stirred for 2 hours. 17.1 g (corresponding to 3% by weight) of commercial calcium phosphate powder (Merck, $D_{50}$<2 µm) was subsequently added in portions, based on the total weight of the sol provided (569.5 g). 1% by weight of a dispersant (DB194, anhydrous; Byk Chemie, Wesel) was added for the purposes of dispersion and was stirred for a further 2 hours.

The glass test specimen was subsequently coated by dipping said test specimen with a withdrawal speed of 1.5 mm/s. It was subsequently dried at room temperature for 1 hour and the coating was ceramised (calcined) at 500° C. for 10 minutes. An electron microscope image of the coating is shown in FIG. 2b).

Preparations containing 1% by weight and 8% by weight of calcium phosphate powder instead of 3% calcium phosphate powder were produced in accordance with the above description and were applied to glass. FIGS. 2a) and 2c) are electron microscope images of the coatings with 1% by weight and 8% by weight of calcium phosphate powder respectively.

Coatings were applied to TiA16V4, titanium, a stainless steel and the plastics material polymethyl methacrylate (PMMA) in accordance with Example 1 specified above. The ceramisation step was dispensed with for the PMMA coating, and it was instead annealed at 120° C. for 1 hour after the drying process.

Example 2

Coating with a Titanium Oxide Filler 41.7 g of tetrabutoxy titanate were dissolved in 300 g of n-butanol at room temperature and were stirred for 2 hours. 1.71 g (corresponding to 0.5% by weight), 10.26 g (corresponding to 3% by weight), and 20.52 g (corresponding to 6% by weight), based on the total weight of the sol provided (341.7 g), of commercial titanium oxide powder (Alfa Aesar, Karlsruhe; $D_{50}$: 0.3 µm) were added in portions. 1% by weight of a dispersant (DB194, anhydrous; Byk Chemie, Wesel) was added for the purposes of dispersion and was stirred for a further 2 hours.

The glass test specimen was subsequently coated by means of dipping with a withdrawal speed of 1.5 mm/s. It was subsequently dried at room temperature for 1 hour and the coating was ceramised at 500° C. for 10 minutes. Coatings were applied to TiAl6V4, titanium, a stainless steel, zirconium oxide and the plastics material polymethyl methacrylate (PMMA) in accordance with Example 2 specified above. The ceramisation step was dispensed with for the PMMA coating, and it was instead annealed for 1 hour at 120° C. after the drying process.

Example 3

Description of the Mode of Action

In order to demonstrate the mode of action of the powder-filled coating, glass substrates (plates, diameter 14.5 mm)

were provided with coatings in accordance with Example 1 which contained different amounts of commercial calcium powder (Merck, $D_{50}$<2 μm). The release of calcium under physiological conditions was determined on the one hand and the cell growth on the surfaces obtained was determined as a function of the powder filling on the other.

Calcium Content Measurement:

The calcium concentration was determined by means of a photometric test. This involves the formation of a complex by the reaction of o-cresolphthalein complexone (CPC, Fa. Fluka) with calcium at an alkaline pH. The purple colour of the colour complex formed is measured absorptively at 575 nm. The CPC reagent is prepared as follows: 625 mg of 8-hydroxy quinoline (Fluka) were dissolved in 25 ml dimethyl sulphoxide (Serva), then 10 mg o-cpc and 250 μl 36% HCl (Fluka) were added and were topped up with 250 ml of distilled water. To produce the diethyl amine buffer, 2 ml of diethylamine and 25 mg of KCl were dissolved in 40 ml of distilled water and were then topped up with distilled water to a volume of 50 ml. For the test, 50 μl samples, standard and blanks (pure lysis buffer) were provided in 2.5 ml PS microcells (Brand) and 960 μl of distilled water were added. 1 ml CPC reagent and 1 ml diethylamine buffer were subsequently added in each case by means of a pipette and mixed, and were then measured in a spectrophotometer (Beckmann Coulter) after 5 minutes of incubation. A calcium standard was used to determine the concentration.

Cell Test Conditions:

Culture medium: 90% RPMI 1640 (=2.05 mM glutamine-containing serum), 10% FCS (fetal calf serum); incubation: 48 h, 37° C., 5% CO2, static culture, darkness)

Cell lines: MC3T3-E1 (foetal mouse osteoblasts)

Culture: 24-well petri dishes, polystyrene

Inoculum: 120,000 cells/ml and well, 1 g phase

Cell proliferation: trypsinisation (300 μl of trypsin EDTA) for a period of 8 minutes in an incubator shaker at 37° C., the enzyme reaction stopped with 700 μl of culture medium. Cell count measured in a Coulter counter.

Mitochondrial activity: WST test (Roche, Mannheim)

FIG. 3 shows that the amount of calcium released increases proportionally with the powder filling. This also indicates that despite the fact that the fillers are bound in a mechanically fixed manner in the matrix, an exchange occurs with the surrounding medium and active ingredients become active through the sol-gel matrix. A comparison of the release of calcium ions (FIG. 3) and the cell tests (FIG. 4) clearly shows that the cell growth is proportional to the release of calcium from the coating. From a powder content of 6% by weight upwards, saturation is reached and cell growth is not stimulated further. The transition into a plateau demonstrates, however, that the effect relates only to the released calcium ions and not to the change in morphology caused by the different amounts of powder, since otherwise a significant increase in the cell count would have been observed between 6 and 8% by weight of filler.

FIG. 6 shows the change in the cell count and mitochondrial activity as a function of the amount of powder introduced. Since no active substances are released in the case of the titanium oxide filer, the different rates of cell growth are caused according to the invention by the change in the surface morphology. The different surface textures are shown in FIG. 5. Since it is no longer possible to form a homogeneous layer at a filling degree of 6% by weight of the titanium oxide filler, the cell count and mitochondrial activity decrease accordingly in comparison with the samples filled with only 3% powder.

What is claimed is:

1. Process for preparing an implant with a particle-filled, metal oxide coating, the process comprising:
    (a) providing a mixture of an organic solvent and an organometallic precursor, wherein the organic solvent and the organometallic precursor are present in the mixture in the form of a sol;
    (b) adding a particle-shaped filler having a particle size between 0.1 and 10 μm to the mixture of step (a) to produce a preparation, wherein the amount of the particle-shaped filler added does not exceed 15% by weight of the total weight of the mixture;
    (c) applying the preparation of step (b) to an implant to provide a coating on the implant; and
    (d) drying the coating applied,
    wherein steps (a)-(d) are performed one or more times, with each iteration of step (b) employing a different particle-shaped filler, a different concentration of the particle-shaped filler, or both, whereby an implant with a particle-filled, metal oxide coating is prepared having a surface $R_a$ value of 0.01 to 10 μm, optionally 0.1 to 5 μm, and further optionally 0.2 to 1.5 μm.

2. Process according to claim 1, wherein the mixture additionally contains water, a mineral acid, an organic acid, or a combination thereof.

3. Process according to claim 2, wherein the mineral acid is selected from the group consisting of nitric acid, hydrochloric acid, sulfuric acid, phosphoric acid, and mixtures thereof.

4. Process according to claim 2, wherein the organic acid is selected from the group consisting of citric acid, trifluoroacetic acid, acetic acid, and mixtures thereof.

5. Process according to claim 1, wherein the mixture further contains a dispersant.

6. Process according to claim 1, wherein the solvent is a linear or branched $C_2$-$C_8$ alcohol a cyclic, aromatic, or heteroaromatic carbohydrate or a mixture thereof.

7. Process according to claim 1, wherein the organometallic precursor is an organometallic compound with a multicoordinated metal atom having one or more —OR ligands coordinated to the metal atom by the oxygen atom of the —OR, wherein R is a $C_2$-$C_8$ alkyl or alkylene residue optionally interrupted or substituted by one or more oxygen atoms, nitrogen atoms, or a combination thereof.

8. Process according to claim 7, wherein the organometallic precursor is selected from the group consisting of tetraethoxy titanate, tetra(n-propoxy) titanate, tetra(isopropoxy) titanate, tetra(n-butoxy) titanate, tetra(isobutoxy) titanate, tetra(tert-butoxy) titanate, tetraethoxy orthosilicate, tetra(n-butoxy) orthosilicate, tetra(isobutoxy) orthosilicate and tetra (tert-butoxy) orthosilicate.

9. Process according to claim 1, wherein the metal atom of the organometallic precursor is selected from the elements titanium, silicon, aluminum and zirconium.

10. Process according to claim 1, wherein the filler is formed from metals, metal alloys, plastics materials, glass, ceramics, composite materials, sparingly soluble salts, or a mixture thereof.

11. Process according to claim 1, wherein the filler may release an active substance under physiological conditions.

12. Process according to claim 11, wherein the active ingredient is an ion, or a therapeutically active substance.

13. Process according to claim 12, wherein the ion is a calcium, zinc, silver, copper or magnesium ion.

14. Process according to claim 1, wherein the implant is a catheter, an osteosynthesis plate, an endoprosthesis, an external fixator, an internal fixator, a nail, a screw, a wire, a heart valve, a synthetic blood vessel, a shunt, a facial surgery/plastic implant, a middle ear implant or a dental implant.

15. Process according to claim 1, wherein the implant is formed from a metal, a metal alloy, a glass, a ceramic, a plastics material, a composite material or a bone substitute material.

16. Process according to claim 15, wherein:
(i) the metal or metal alloy is selected from the group consisting of titanium; steel; iron; a steel, iron, titanium, or CoCr alloy, or a combination thereof; and an osteosynthesis steel; or
(ii) the plastics material is selected from the group consisting of a polyethylene, a polypropylene, a polytetrafluoroethylene, a polyethylene terephthalate, a polyamide, a polyurethane, a polysiloxane, a polysiloxane elastomer, a polyetheretherketone, a polysulphone, a polysaccharide, a polylactide or a combination thereof.

17. Process according to claim 1, wherein the applying step comprises dip coating, spin coating, applying by doctor blade, printing or spraying the preparation.

18. Process according to claim 1, wherein the drying step is carried out in air, in an inert gas atmosphere, or under supercritical drying conditions.

19. Process according to claim 1, further comprising (e) heating the coating applied in step (c) to between 100 and 1000° C. after step (d).

20. Process according to claim 1, wherein the applying step comprises applying the preparation in the form of a sol in which the filler is dispersed homogeneously, wherein during or after the applying step, the sol changes into a gel in which the filler is homogeneously dispersed.

21. Process according to claim 1, wherein the applying step comprises applying the preparation in an amount such that after the drying step, the coating has a layer thickness that is between 50 and 1000 nm.

22. Process according to claim 1, wherein in one or more iterations of step (b), a different concentration of particle-shaped filler is employed such that the different coatings obtained contain different concentrations of the particle-shaped filler.

23. Process according to claim 1 or claim 22, wherein in one or more iterations of step (b), a different particle-shaped filler is employed such that the different coatings obtained contain different particle-shaped fillers.

24. Implant with a coating produced according to the process of claim 1.

25. Implant according to claim 24, wherein the implant further comprises one or more active substances contained in the coating that can be eluted into the surrounding medium under physiological conditions.

26. Implant according to claim 24 or claim 25, wherein the coating has a thickness of between 50 and 1000 nm.

27. Implant according to claim 24, wherein the fillers in each coating are homogeneously dispersed.

28. Implant according to claim 27, wherein the fillers contained in the coating contain calcium, zinc, silver, copper, magnesium ions or a combination thereof.

29. Process according to claim 6, wherein the linear or branched $C_2$-$C_8$ alcohol is selected from the group consisting of methanol, ethanol, n-propanol, isopropanol, n-butanol, isobutanol, and tert-butanol.

30. Process according to claim 6, wherein the solvent is benzene or toluene.

31. Process according to claim 10, wherein the filler comprises a glass ceramic.

32. Process according to claim 18, wherein the inert gas atmosphere is a nitrogen atmosphere or a noble gas atmosphere.

33. Process according to claim 21, wherein after the drying step, the coating has a layer thickness that is between 50 and 500 nm.

34. Process according to claim 33, wherein after the drying step, the coating has a layer thickness that is between 150 and 300 nm.

35. Implant according to claim 26, wherein the coating has a layer thickness that is between 50 and 500 nm.

36. Process according to claim 35, wherein the coating has a layer thickness that is between 150 and 300 nm.

* * * * *